United States Patent [19]

Rettig et al.

[11] Patent Number: 4,851,332

[45] Date of Patent: Jul. 25, 1989

[54] CHORIOCARCINOMA MONOCLONAL ANTIBODIES AND ANTIBODY PANELS

[75] Inventors: Wolfgang J. Rettig; Carlos Cordon-Cardo, both of New York, N.Y.; John P. Koulos, Farmington, Conn.; John L. Lewis, Jr., New York, N.Y.; Herbert F. Oettgen, New Canaan, Conn.; Lloyd J. Old, New York, N.Y.

[73] Assignee: Sloan-Kettering Institute for Cancer Research, New York, N.Y.

[21] Appl. No.: 718,162

[22] Filed: Apr. 1, 1985

[51] Int. Cl.$^4$ .................... G01N 33/535; C12N 5/00; C07K 15/04

[52] U.S. Cl. ........................................ 435/7; 530/387; 424/85; 436/548; 935/104; 935/107; 935/110; 435/68; 435/70; 435/172.2; 435/240.27

[58] Field of Search ................ 435/240, 241, 948, 68, 435/70, 172, 2, 7; 935/104, 107, 110; 424/85; 530/387, 388; 436/548; 240/27

[56] References Cited

U.S. PATENT DOCUMENTS 4,558,035 12/1985 Johnson ................................ 514/8
4,643,971 2/1987 Fradet .............................. 435/24 D

OTHER PUBLICATIONS

Battifora H. et al., Cancer 54(5): 843–848(1984) cited in Biosis Abstract 85:225491.

Paiva, J. et al., Am. J. Pathol 111(2):156–165(1983) cited in Biosis Abstract 83: 308790.

Primary Examiner—Margaret Moskowitz
Attorney, Agent, or Firm—John P. White

[57] ABSTRACT

Monoclonal antibodies to specific cell surface antigens of human choriocarcinoma, teratocarcinoma, and normal trophoblasts are disclosed. Additionally, panels of monoclonal antibodies which may be used in phenotyping cell and tissue samples are disclosed as well.

4 Claims, 7 Drawing Sheets

FIGURE 3

Monoclonal Antibody

| Cell line | Origin | LK26 | SV19 | K8 | SV63 | LK24 | K66 | S4 |
|---|---|---|---|---|---|---|---|---|
| GCC-SV(c) | Gestational chorioca. | 1000 | 1000 | 1500 | 2500 | 250 | - | 100 |
| Lu-75(c) | Gestational chorioca. | 150 | 150 | 10 | 10 | 50 | 150 | 25 |
| BeWo | Gestational chorioca. | 500 | 50 | 1000 | 1500 | 150 | 50 | 25 |
| JEG-3 | Gestational chorioca. | 150 | 150 | 10 | 1000 | 50 | - | 1 |
| JAR | Gestational chorioca. | 150 | 50 | - | 50 | 150 | - | |
| SCH | Gastric chorioca. | 1000 | 50 | - | 50 | - | - | 250 |
| OCC-MM | Ovarian chorioca. | 500 | 25 | - | 10 | 50 | 3000 | 250 |

FIGURE 4A

Monoclonal Antibody

| Cell lines | LK26 | SV19 | K8 | SV63 | LK24 | K66 |
|---|---|---|---|---|---|---|
| Choriocarcinoma | | | | | | |
| GCC-SV(c),LU-75(c),BeWo, JAR | ●●●●● | ●●●●● | ●●●○● | ●●●●● | ●●●●● | ○●●○○ |
| JEG-3,OCC-MM,SCH | ●● | ●● | ○○ | ●● | ●○ | ●○ |
| Teratocarcinoma | | | | | | |
| Tera-1,-2,833KE,577MF | ●●●○ | ●●●○ | ●●●○ | ●●●○ | ○○○○ | ○○●○ |
| Breast cancer | | | | | | |
| MCF-7,Cama,AlAb, ZR75.1, | ●○○○○ | ●●○○○ | ○○○○○ | ○○○○● | ●●●●● | ○●○●○ |
| BT-20,-474,SK-BR-5,-7 | ○○●○● | ●○○○○ | ○○○○○ | ○○○○● | ●○○○○ | ●○●●● |
| MDA-48-134,-231 | | | | | | |
| Colon cancer | | | | | | |
| SW-48,-403,-480,-620,-837, | ○○●●○ | ○○○○○ | ○○●○○ | ○○●●● | ○●●○○ | ●●●●● |
| SW-1083,-1116,-1222,-1217, | ○○○○○ | ○○○○○ | ○●○○○ | ○●○○○ | ○○○○○ | ●○○○○ |
| SC-40-10,-11,-13,-15,HT29 | ○○○○ | ○○○○ | ○○○○ | ●○○○ | ○○●○ | ●○●● |
| Ovarian, uterine cancer | | | | | | |
| SK-V08,-2774,A10,ROAC, | ●○●○○ | ○○○○○ | ●○●○○ | ●○●○○ | ○○●○● | ●●●○○ |
| SW626,KD-UT-1,ME180 | ●○ | ○○ | ○○ | ○○ | ○○ | ○○ |
| Bladder cancer | | | | | | |
| TCCSUP,253J,T24,RT4,486P, | ○○○○○ | ○○○○○ | ○○○○○ | ○○○○● | ○○○○○ | ●●●○○ |
| VM-CUB-1,-2,-3,639V,647V, | ●○○○● | ○○○○○ | ○○○○○ | ●○●○● | ○○○○○ | ●●●●● |
| SW-800,-1710,575A,SCABER | ○●○○ | ○○○○ | ○○○○ | ○○○○ | ○○○○ | ●●●● |
| Renal cancer | | | | | | |
| SK-RC-1,-2,-4,-6,-7, | ●●●●● | ○○○○○ | ○○○○○ | ○○○○○ | ○○○○○ | ●●●●● |
| SK-RC-8,-9,-20,-29,-31, | ●●●●● | ○○○○○ | ○○○○○ | ○○○○○ | ○○○●○ | ●●●●● |
| SK-RC-34,-39,-41,-44,-45 | ●●●●● | ○○○○○ | ○○○○○ | ○○○○○ | ○●○●○ | ●●●●● |

FIGURE 4B

| | | | | | | |
|---|---|---|---|---|---|---|
| Prostrate cancer | | | | | | |
| DU-145,KNS-62 | 00 | 00 | 00 | 00 | 00 | ●0 |
| Lung cancer | | | | | | |
| SK-LC-1,-2,05,06,-7, | ●0●●0 | 00000 | 00000 | 00000 | 0●0●● | ●0●00 |
| SK-LC-8,-12,-14,-16,-17 | 00●00 | 00000 | 00000 | 00000 | ●0000 | 000●● |
| Pancreas, hepatic cancer | | | | | | |
| Capan-1,-2,AsPc-1,SK-HEP-1 | 0●00 | 0000 | 0000 | ●●●0 | 0000 | ●●●● |
| Melanoma | | | | | | |
| SK-MEL-12,-23,-28,-29,-31, | 00000 | 00000 | 00000 | 00000 | 00000 | 00000 |
| SK-MEL-37,-41,-94,-147,-153 | 00000 | 00000 | 00000 | 00000 | 00000 | 0●000 |
| Astrocytoma | | | | | | |
| SK-MG-1,-2,-3,-14,-6, | 00000 | 00000 | 00000 | 00000 | 00000 | ●00●0 |
| SK-MG-7,-9,-12,-13,-17 | 00000 | 00000 | 00000 | 00000 | 00000 | 0●●●0 |
| Neuroblastoma | | | | | | |
| SK-N-SH,-MC,-BE(1),-BE(2) | 0000 | 0000 | 0000 | 0000 | 0000 | 0000 |
| Leukemia, lymphoma | | | | | | |
| MOLT-4,T45,HPB-ALL,212, | 00000 | 00000 | 00000 | 00000 | ●●●●0 | 00000 |
| SK-DHL-2,-10,SK-LY-16,-18, | 00000 | 00000 | 00000 | 00000 | 00000 | 00000 |
| RAJI,BALL-1,ARA-10,NALL-1, | 00000 | 00000 | 00000 | 00000 | 00●●● | 00000 |
| NKL-1,-2,NALM-1,-16,HL-60, | 00000 | 00000 | 00000 | 00000 | 0●000 | 00000 |
| K562,SK-MY-1,U937 | | | | | | |
| Normal cells | | | | | | |
| Kidney epithelium | 00000 | 00000 | 00000 | 00000 | 00000 | ●●●●● |
| Skin fibroblasts | 00000 | 00000 | 00000 | 00000 | 00000 | 00000 |
| EBV-transformed B cells | 00000 | 00000 | 00000 | 00000 | ●●●00 | 00000 |
| Erythrocytes (A,B,O) | 000 | 000 | 000 | 000 | 00● | 000 |

FIGURE 4C

| Cell Type | Monoclonal Antibody | | | | | |
|---|---|---|---|---|---|---|
| | LK26 | SV19 | K8 | SV63 | LK24 | K66 |
| Choriocarcinoma | ●●●●● ●● | ●●●●● ●● | ●●●○○ ○○ | ●●●●● ●● | ●●●●● ●○ | ●○○○● ●○ |
| Teratocarcinoma | ●●●● | ●●●○ | ●●●○ | ●●●○ | ○○○○ | ○○●○ |
| Breast cancer | ●○○○○ | ●●●○○ | ○○○○○ | ○○○○● | ●●●●● | ●●●○○ |
| Colon cancer | ○○○○○ | ○○○○○ | ●○○○○ | ●○○○○ | ○○○○○ | ○●○○○ |
| Ovary/uterus cancer | ●○○○○ | ○○○○○ | ●○○○○ | ●○○○○ | ○●○○○ | ●○●○○ |
| Bladder cancer | ○○○○○ | ○○○○○ | ○○○○○ | ○○○○● | ○○○○○ | ●●●○○ |
| Renal cancer | ●●●●● | ○○○○○ | ○○○○○ | ○○○○○ | ○○○○○ | ●●●●● |
| Lung cancer | ●○○○○ | ○○○○○ | ○○○○○ | ○○○○○ | ●○○○○ | ○○○●● |
| Melanoma | ○○○○○ | ○○○○○ | ○○○○○ | ○○○○○ | ○○○○○ | ○○○○○ |
| Astrocytoma | ○○○○○ | ○○○○○ | ○○○○○ | ○○○○○ | ○○○○○ | ●●○○○ |
| Neuroblastoma | ○○○○○ | ○○○○○ | ○○○○○ | ○○○○○ | ○○○○○ | ○○○○○ |
| Leukemia/lymphoma | ○○○○○ ○○○○○ | ○○○○○ ○○○○○ | ○○○○○ ○○○○○ | ○○○○○ ○○○○○ | ●●●●● ○○○○○ | ○○○○○ ○○○○○ |
| EBV$^+$ B cells | ○○○○○ | ○○○○○ | ○○○○○ | ○○○○○ | ●●●○○ | ○○○○○ |
| Skin fibroblasts | ○○○○○ | ○○○○○ | ○○○○○ | ○○○○○ | ○○○○○ | ○○○○○ |
| Kidney epithelium | ○○○○○ | ○○○○○ | ○○○○○ | ○○○○○ | ○○○○○ | ●●●●● |
| Erythrocytes (A,B,O) | ○○○ | ○○○ | ○○○ | ○○○ | ○○● | ○○○ |

FIGURE 5

| Tissue | LK26 A | LK26 F | SV19 A | SV19 F | K8 A | K8 F | SV63 A | SV63 F | LK24 A | LK24 F | K66 A | K66 F |
|---|---|---|---|---|---|---|---|---|---|---|---|---|
| Placenta 14 weeks | ● | | ● | | ● | | ● | | ● | | 0 | |
| 40 weeks | ● | | ● | | ● | | ● | | ● | | 0 | |
| Mammary gland | 0 | | ● | | 0 | | 0 | | 0 | | 0 | |
| Colon | 0 | 0 | ● | ● | 0 | 0 | ● | ● | ● | ● | 0 | 0 |
| Testis | 0 | 0 | 0 | 0 | 0 | 0 | ● | ● | 0 | 0 | 0 | 0 |
| Ovary | 0 | 0 | 0 | 0 | 0 | 0 | ● | ● | 0 | 0 | 0 | 0 |
| Uterus/Cervix | 0 | | 0 | | 0 | | 0 | | 0 | | 0 | |
| Fallopian tube | 0 | | 0 | | 0 | | 0 | | 0 | | 0 | |
| Kidney | 0 | 0 | 0 | 0 | 0 | 0 | 0 | 0 | ● | ● | 0 | 0 |
| Urothelium | 0 | 0 | 0 | 0 | 0 | 0 | 0 | 0 | ● | ● | 0 | 0 |
| Liver | 0 | 0 | 0 | 0 | 0 | 0 | 0 | 0 | 0 | 0 | 0 | 0 |
| Pancreas | 0 | 0 | 0 | 0 | 0 | 0 | 0 | 0 | 0 | 0 | 0 | 0 |
| Lung | 0 | 0 | 0 | 0 | 0 | 0 | 0 | 0 | 0 | 0 | 0 | 0 |
| Bronchus | 0 | 0 | 0 | 0 | 0 | 0 | 0 | 0 | 0 | 0 | 0 | 0 |
| Adrenal gland | 0 | 0 | 0 | 0 | 0 | 0 | 0 | 0 | 0 | 0 | 0 | 0 |
| Thyroid gland | 0 | 0 | 0 | 0 | 0 | 0 | 0 | 0 | 0 | 0 | 0 | 0 |
| Thymus | | 0 | | 0 | | 0 | | 0 | | ● | | 0 |
| Spleen | 0 | 0 | 0 | 0 | 0 | 0 | 0 | 0 | 0 | 0 | 0 | 0 |
| Lymph node | 0 | 0 | 0 | 0 | 0 | 0 | 0 | 0 | 0 | 0 | 0 | 0 |
| Skin | 0 | 0 | 0 | 0 | 0 | 0 | 0 | 0 | 0 | 0 | 0 | 0 |
| Heart/Blood vessel | 0 | 0 | 0 | 0 | 0 | 0 | 0 | 0 | 0 | 0 | 0 | 0 |
| Nervous system | 0 | 0 | 0 | 0 | 0 | 0 | 0 | 0 | 0 | 0 | 0 | 0 |

CHORIOCARCINOMA MONOCLONAL ANTIBODIES AND ANTIBODY PANELS

FIELD OF THE INVENTION

This invention relates to new monoclonal antibodies which are specific to surface glycoproteins of cultured choriocarcinoma and teratocarcinoma cells, and choriocarcinoma and teratocarcinoma tumor tissues. Additionally, the invention relates to panels of monoclonal antibodies which are used to phenotype these cultured cells and tumor tissues.

PRIOR ART

Surface antigens are expressed on the surface of normal and malignant cells, and have been used to probe molecular events that occur during cellular differentiation, or that accompany malignant transformation. Lloyd, K. O. "Human Tumor Antigens: Detection and Characterization with Monoclonal Antibodies" in R. B. Herberman, ed., *Basic and Clinical Tumor Immunology*, pp. 159-214 (Martinus Nytoff, Boston (1983).

Earlier studies have used monoclonal antibodies to detect surface antigens of different types of cancer, e.g., Dippold, et al, Proc. Natl. Acad. Sci., U.S.A. 77, 6114–6118 (1980) (melanoma); Cairncross, et al, Proc. Natl. Acad. Sci., U.S.A. 79, 5641–5645 (1982) (astrocytoma); Ueda et al, Proc. Natl. Acad. Sci., U.S.A. 78, 5122–5126 (1981) (renal cancer); Fradet et al, Proc. Natl. Acad. Sci., U.S.A. 81, 224–228 (1984) (bladder cancer); and Mattes et al, Proc. Natl. Acad. Sci., U.S.A. 81, 568–572 (1984) (ovarian cancer). While there are several reports in the literature of monoclonal antibodies used to describe trophoblast and choriocarcinoma cell surface antigens, e.g., Lipinski, et al., Proc. Natl. Acad. Sci., U.S.A. 78 5147–5150 (1981); Sunderland, et al., Immunol. 43 541–546 (1981); McLaughlin, et al., Int. J. Cancer 30 21–26 (1982); Travers, et al., Int. J. Cancer 33 633–641 (1984), none of these describe antigens binding to monoclonal antibodies LK26, LK24, K66, S4 or SV19. Other monoclonal antibodies to placental alkaline phosphatase are disclosed but not SV63 or K8.

BACKGROUND OF THE INVENTION

The introduction by Köhler and Millstein in 1975 of a revolutionary new procedure for the routine production of monoclonal antibodies using hybridomas allows the production of almost unlimited quantities of antibodies of precise and reproducible specificity. While conventional antisera produced by immunizing animals with tumor cells or other antigens contain a myriad of different antibodies differing in their specificity and properties, hybridomas produce a single antibody with uniform characteristics. The Köhler-Millstein procedure entails the fusion of spleen cells from an immunized animal with an immortal myeloma cell line. From the fused cells (hybridomas), clones are selected that produce antibody of the desired specificity. As hybridoma cells can be cultured indefinitely (or stored frozen in liquid nitrogen), a constant supply of antibody is assured.

Antibodies are proteins that have the ability to combine with and recognize other molecules, known as antigens. Monoclonal antibodies are not different from other antibodies except that they are very uniform in their properties and recognize only one antigen or a portion of an antigen known as a determinant.

In the case of cells, the determinant recognized is an antigen on or in the cell which reacts with the antibody. It is through these cell antigens that a particular antibody recognizes, i.e., reacts with, a particular kind of cell. Thus the cell antigens are markers by which the cell is identified.

Antigenic markers may be used to observe normal processes of cell differentiation and to locate abnormalities, such as cancer, within a given cell system. The process of differentiation is accomplished by changes in the surface antigenic phenotype, and antigens that distinguish cells at different phases, or transformed cells, may be observed if a correct antibody is available.

Transformation of normal cells into carcinogenic tumor cells is accompanied by changes in surface protein phenotypes. Monoclonal antibodies specific for surface proteins of carcinogenic cells may be used to identify those cells. Additionally, different cancers exhibit different surface protein phenotypes. Hence, it is possible to determine the presence of a particular type of cancer, given the proper monoclonal antibodies.

By means of the monoclonal antibodies of this invention, it is possible to identify choriocarcinoma and teratocarcinoma cells and tissues, utilizing the specificity of monoclonal antibodies to the cell surface markers of these carcinogenic cells and tissues. Choriocarcinomas are cancers which result from transformation of trophoblasts (in the case of gestational choriocarcinomas) or from transformation of germ cells (in the case of germ cell tumors). The transformation alters the surface antigens of the resulting choriocarcinoma, enabling one to distinguish between cancerous and noncancerous materials.

Panels of monoclonal antibodies are provided which phenotypically identify choriocarcinoma and teratocarcinoma cells and tissues.

BRIEF DESCRIPTION OF THE FIGURES

FIG. 3: Antigen Distribution. Serial dilutions of antibody were tested by MHA assays and the numbers indicate the reciprocal of the highest antibody dilution ($\times 10^{-3}$) giving rosette formation. Dashes indicate negative reactions at the starting dilution of antibody (1/250 nu/nu mouse serum).

FIG. 4: Reactivity of Monoclonal Antibodies to Cell Surface Antigens of Cultured Human Cells and Cell Lines. Serial dilutions of antibody were tested by MHA assays. Reactivity with the cell lines shown is as follows:
- ● positive reaction with titration endpoint of $1 \times 10^{-4} - 1 \times 10^{-5}$;
- ◒ positive reaction with titration endpoint of $4 \times 10^{-3} - 1 \times 10^{-4}$;
- ○ no reactivity at starting dilution of antibody (i.e., 1/250 mouse serum).

Figure 1:
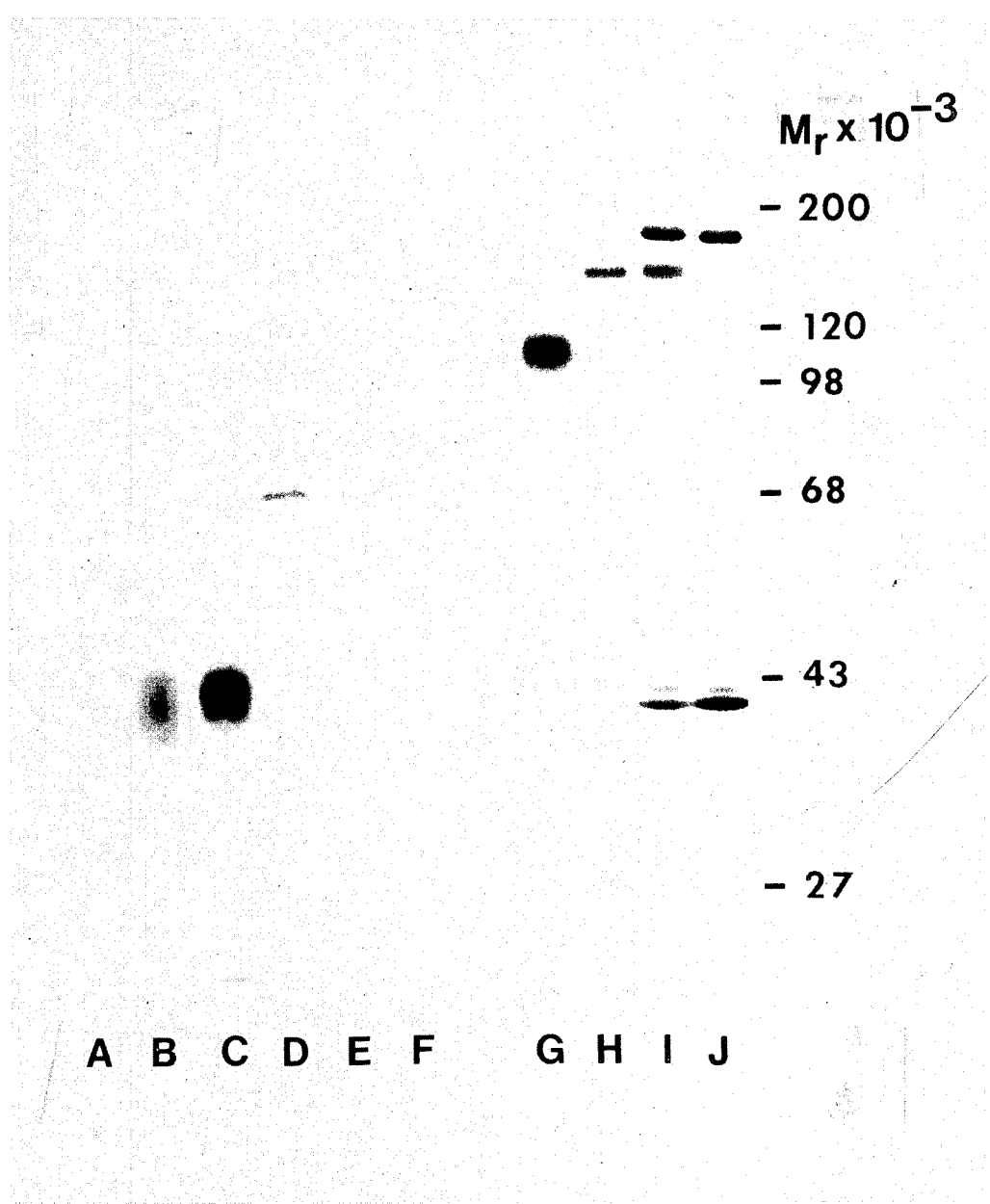
FIG. 1. Fluorogram of immunoprecipitates obtained with monoclonal antibodies to cell surface antigens using extracts of [$^{35}$S]methionine-labelled choriocarcinoma cells GCC-SV(c). Con A bound fractions of extract were used for experiments A–H and unfractionated extracts for experiments I and J. Immunoprecipitates were separated on 9% SDS-NaDodSO$_4$/polyacrylamide gels. Monoclonal antibodies used for immunoprecipitation tests were—Lane A: normal nu/nu mouse serum; Lane B: AbLK26; Lane C: AbSV19; Lane D: AbSV63; Lane E: AbK8; Lane F: AbSV63 (cell extract precleared with AbK8); Lane G: AbSV13; Lane H: AbS4; Lane I: AbS4; Lane J: normal nu/nu mouse serum. Position of molecular weight markers is indicated on the right.

Note that LK24 reactivity is restricted to a small fraction (5-20%) of the cells in the cultures.

Human erythrocytes were tested by absorption analysis and hemagglutination tests. AbLK24 reacted with type "O" erythrocytes in absorption tests, but did not produce hemagglutination.

FIG. 5: Immunofluorescence Analysis of Human Adult (A) and Fetal (F) Tissues with Monoclonal Antibodies to Cell Surface Antigens.
- ● positive reaction
- ◒ positive reaction with a subpopulation of cells
- ○ no reactivity Note that SV63 reactivity was restricted to germ cells in the testis and ovary tissue examined.

Note that LK24 reactivity was restricted to distal and collection tubules in the kidney tissue examined.

FIG. 6: Immunofluorescence Analysis of Human Tumor Tissues with Monoclonal Antibodies.
- ● positive reaction
- ◒ positive reaction with a subpopulation of cells
- ○ no reactivity Note that SV63 reactivity was restricted to germ cells in the testis and ovary tissue examined.

Note that LK24 reactivity was restricted to distal and collection tubules in the kidney tissue examined.

FIG. 7: Reactivity of Monoclonal Antibodies to Choriocarcinoma Antigens with Human Breast Cancer Lines. Results of MHA assays are indicated as follows:
- +++ positive reaction in MHA direct test with titration endpoint of $1 \times 10^{-4} - 1 \times 10^{-7}$;
- ++ positive reaction in MHA direct test with titration endpoint of $4 \times 10^{-3} - 1 \times 10^{-4}$;
- + positive reaction in absorption tests, but not in MHA direct tests;
- − negative reaction in both direct test and absorption analysis.

FIG. 8: Comparison of Monoclonal to Trophoblast Antigens. Cell lines were tests by MHA assays. Reactivity is indicated by filled or semi-filled circles, following FIG. 4. NDOG-1 and NDOG-2 were tested as hybridoma supernatants at 1000-fold lower dilutions. For Trop-1 and Trop-2 ascites fluid from hybrid clones 162-21.2 and 162.46.2 as in Lipinski, Proc. Natl. Acad. Sci., U.S.A 78 5147-5150 (1981) were used.

DETAILED DESCRIPTION OF PREFERRED EMBODIMENTS

The Hybridomas and Monoclonal Antibodies

Hybridoma cell lines producing the monoclonal antibodies of the present invention have been deposited prior to the filing of the present application at the American Type Culture Collection, 12301 Parklawn Drive, Rockville, Md. 20852 and will be made available to the public during the pendency of any patent issuing therefrom, in accordance with the Budapest Treaty. The monoclonal antibodies bear the following designations:

| Herein Designated | ATCC | Date of Deposit |
| --- | --- | --- |
| LK26 | HB 8764 | March 29, 1985 |
| SV19 | HB 8557 | May 4, 1984 |
| K8 | HB 8765 | March 29, 1985 |
| SV63 | HB 8766 | March 29, 1985 |
| LK24 | HB 8769 | March 29, 1985 |
| K66 | HB 8767 | March 29, 1985 |

Deposit is for the purpose of enablement only and is not intended to limit the scope of the present invention. Clones of these cell lines and other cell lines derived therefrom are considered to be foreseen by the present invention.

Cell Lines and Cell Culture

Human gestational choriocarcinoma cell lines GCC-SV(c) and Lu-75(c), as reported by Kim et al, Gynecol. Oncol. 6, 165-182 (1978); BeWo, JEG, and JAR were used. The cell line OCC-MM(c), established from a heterotransplant of human ovarian choriocarcinoma propagated in nu/nu mice, as reported by Kim, supra, SCH, a choriocarcinoma derived from gastric tumor and described by Kameya et al, Cancer Res., 35 2025-2032 (1975), were used as well, in immunization. Other tumor cell lines, short-term cultures of human skin and lung fibroblasts, and kidney epithelial cells were taken from Sloan-Kettering Institute's tissue bank. The tissue culture technique described by Carey et al, Proc. Natl. Acad. Sci., U.S.A. 73, 3278-3282 1 (1976) was used.

IMMUNIZATION AND GENERATION OF MONOCLONAL ANTIBODIES (BALB/c X C57BL/6) F1 mice were immunized by intraperitoneal injection of cultured choriocarcinoma cells to produce hybridomas generating monoclonal antibodies as follows:

| Immunizing Cell Line | Monoclonal Antibody |
| --- | --- |
| GCC-SV(c) | SV19 |
| GCC-SV(c) | SV63 |
| LU-75(c) | LK24 |
| LU-75(c) | LK26 |
| OCC-MM | K66 |
| placental membrane | K8 |

The method of immunization follows Dippold et al, Proc. Natl. Acad. Sci., U.S.A. 77, 6114-6118 (1980).

Spleen cells were then fused with cells of the mouse myeloma cell line MOPC-21 NS/1, and antibody producing clones were then isolated by repeated subcloning. Hybridoma cells were injected, subcutaneously or intraperitoneally, into nu/nu mice (Swiss background), and ascites fluid and serum of mice with progressively growing tumors was used as a source of antibody for serological and biochemical studies, with cultured cells. Antibody subclass was determined by double diffusion in agar, with anti-Ig heavy chain specific antisera.

ASSAYS

I. Serological assays with cultured cells

Mixed hemadsorption (MHA) rosetting assays for the detection of cell surface antigens on cultured cells using rabbit anti-mouse Ig or goat anti-mouse u chain antibodies conjugated to human O erythrocytes, were performed according to methods described by Mattes et al, Proc. Natl. Acad. Sci., U.S.A., 81, 568–572 (1984). Nonadherent target cells were prepared for the MHA assays by the concanavalin A method of Mattes et al, J. Immunol. Meth. 61, 145–150, (1983). Absorption tests and hemagglutination assays with type A, B, AB, O and neuraminidase-treated O erythrocytes were performed as described by Anger et al, Hybridoma 1, 139–146 (1982). Heat stability of antigenic determinants was assessed by heating target cells to 100° C. for 5 minutes prior to absorption tests. Susceptibility of antigenic determinants to enzyme digestion was determined by incubation of target cells with 0.5 mg/ml trypsin in DPBS (Dulbecco's phosphate-buffered saline) for 30 minutes at 37° C. before absorption tests.

II. Immunofluorescence assays of tissue sections

Frozen sections (5 m) of tissues were air-dried, fixed for 10 minutes in 3.7% formaldehyde in phosphate-buffered saline (PBS; 0.01M sodium phosphate, 0.15M NaCl, pH 7.3), washed, and incubated for 1 hour at room temperature with undiluted hybridoma culture supernatant or a 1/50 dilution of nu/nu mouse serum. The slides were washed and incubated for 45 minutes at room temperature with a 1/40 dilution of fluorescein-conjugated goat-anti-mouse Ig, washed again, and wet-mounted in 90% glycerol in PBS.

III. Enzyme-linked immunosorbent-assay

Purified blood group glycoproteins and glycolipids carrying A, B, H, I. Le$^a$, Le$^b$, X and Y structures were adsorbed to the wells of Terasaki plates and enzyme-linked immunosorbent-assays (ELISA) were performed as described by Lloyd et al, in Basic and Clinical Tumor Immunolgy, pp. 159–214 (Martinus Nijhoff, Boston 1983).

IV. Alkaline phosphatase binding assay

Rabbit anti-mouse IgG at a 1/100 dilution in DPBS was adsorbed to the wells of Terasaki plates (1 hour at 4° C.), plates were washed five times with BSA-DPBS (DPBS containing 10 mg/ml bovine serum albumin, fraction V), and incubated with antibodies AbSV63, AbK8, AbSV19, AbSV13 or AbLK26 (1/100 diluted nu/nu sera in BSA-DPBS) for 1 hour at 4° C. Plates were washed five times (BSA-DPBS) and 10 ul/well of a serial dilution of Nonidet-P40 solubilized GCC-SV(c) cell extracts (1–125 ug/ml protein as determined by the Lowry method) was added. Following incubation for 1 hour at 4° C., plates were washed five times (BSA-DPBS). Bound alkaline phosphatase activity was determined after incubation with p-Nitrophenylphosphate (1 mg/ml in 10% diethanolamine buffer, pH 9.7; 30 minutes at 37° C.) by measuring the change in optical density at 405 nm.

V. Immunoprecipitation procedure

Cells were metabolically labeled with [$^3$H]glucosamine or [$^{35}$S]methionine and extracted in Nonidet P-40 buffer following the procedures of Ueda, et al., Proc. Natl. Acad. Sci., U.S.A. 78, 5122–5126 (1981). Fractionation of lysates on concanavalin A (Con A)-Sepharose, immunoprecipitation and NaDodSO4/polyacrylamide gel electrophoresis (SDS-PAGE) procedures have been described by this reference as well. [$^{35}$S]methionine-labeling of cells in the presence of tunicamycin (final concentration 5 ug/ml) was carried out as described by Albino et al, J. Immunol. 131, 1595–1599 (1983).

RESULTS

Six distinct cell surface antigens of human choriocarcinoma were characterized with seven different mouse monoclonal antibodies. Six of the antibodies were generated following immunizations with cultured choriocarcinoma cells or a placenta extract: AbLK26 (IgG2a), AbSV19 (IgG2a), AbK8 (IgG1), AbSV63 (IgG1), AbLK24 (IgM), and AbK66 (IgG2a). Antigen distribution was determined by MHA assays and/or absorption tests with a panel of 150 human cell lines and short-term cultures of fibroblasts and kidney epithelial cells. These results are summarized in FIGS. 3 and 4. Additionally immunofluorescence analyses of a range of normal adult and fetal tissues and tumors are shown in FIGS. 5 and 6. In addition, the choriocarcinoma cell lines used in this study were typed with a series of 20 monoclonal antibodies raised against restricted antigens of other human tumors and the findings with one antibody, AbS4, are presented infra. FIG. 1 shows the results of immunoprecipitation tests with the five antibodies which precipitate glycoproteins from choriocarcinoma cells: LK26 (gp about 30,000 to 35,000), SV19 (gp 40,000 under reduced conditions, 25,000 under unreduced conditions), SV63 and K8 (gp 68,000) and S4 (gp 160,000). A precipitation experiment with AbSV13 which detects a widely distributed glycoprotein (gp 105,000) of human cells as disclosed by Proc. Natl. Acad. Sci., U.S.A. 81, 6437–6441 (1984) and which was used as a negative control in the ALP binding assays, is also shown. Three methods were used to determine whether any of the antibodies recognize blood group antigens: (i) hemagglutination tests, (ii) absorption tests with erythrocytes, and (iii) solid-phase ELISA with purified blood group glycoproteins and glycolipids. Except for AbLK24, the antibodies gave negative results in all three assay systems, indicating that they were unrelated to the A, B, O, I and Lewis blood group structures.

The following is a brief description of the six antigenic systems of human trophoblast and choriocarcinoma described herein.

LK26 antigenic system

LK26 shows a highly restricted distribution. It is expressed on all chloriocarcinoma, teratocarcinoma and renal cancer cell lines. Among the other tumor cell lines tested, only a small subset of epithelial cancer lines bears the LK26 determinant, whereas leukemias, lymphomas and neuroectodermally derived tumors do not. In striking contrast to the positive LK26 phenotype of renal cancer lines, nomral kidney epithelial cells lack LK26 expression. In normal tissues, LK26 is restricted to the trophoblast. All other adult and fetal tissues tested, including normal kidney, were negative for LK26. Studies on gestational chloriocarcinoma and hydatidiform mole tissue show LK26 positivity. A subset of teratocarcinomas, breast and renal cancers was also LK26 positive. In immumoprecipitation tests, AbLK26 precipitated glycoproteins of molecular weight of from about 30,000 to about 35,000 daltons from extracts of

[³H]glucosamine and [³⁵S]methionine-labeled GCC-SV(c) and OCC-MM choriocarcinoma cells.

SV19 antigenic system

SV19 is expressed on 7/7 choriocarcinoma lines (titration endpoints $4 \times 10^{-5}$ to $1 \times 10^{-6}$), ⅜ teratocarcinoma lines, and 4/13 breast cancer lines (titration endpoints $1 \times 10^{-3}$ to $1 \times 10^{-4}$). Over 120 other cell lines were SV19 negative in MHA direct tests. In absorption tests, low levels of SV19 antigen could be detected on 3 additional breast cancer lines and 5/6 colon cancer lines but not on 35 other tumor lines tested by this method (5 renal cancers, 4 bladder cancers, 9 lung cancers, 1 pancreatic cancer, 6 melanomas, 4 astrocytomas, 5 EBV-transformed B cell lines, 1 normal kidney epithelial cell culture). In tissues, SV19 expression is restricted to the normal trophoblast, mammary gland epithelium and colonic epithelium. Among the tumors tested, teratocarcinomas, breast, bladder, colon and lung caners were SV19 positive. In some additional tissues, e.g., fetal testis and fetal ovary, a distinct nuclear staining pattern was found. The relationship between this nuclear reactivity and the cell surface expression of SV19 remains to be determined. In immunoprecipitation tests with extracts of [³H]glucosamine and [³⁵S]methionine-labeled GCCSV(c) cells, AbSV19 detected glycoproteins of molecular weight from about 40 to about 45,000 daltons (under reducing conditions) or molecular weight of about 25,000 daltons (nonreducing conditions).

SV63/K8 antigenic system

Figure 2:
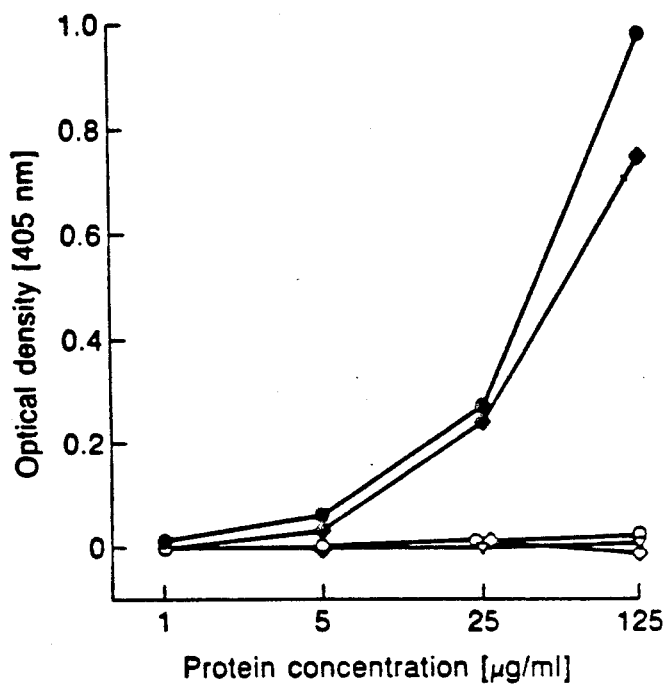
FIG. 2: Analysis of binding of alkaline phosphatase activity by monoclonal antibodies to cell surface glycoproteins of human choriocarcinoma using a solid-phase immunosorbent assay. Serially diluted extracts of GCC-SV(c) cells were used as a source of antigens and total protein concentration of cell extracts is indicated. Five antibodies to glycoproteins of GCC-SV(c) cells were adsorbed to test plates and tested for their ability to bind ALP activity from the extracts. Results of a representative experiment are shown. Antibodies used are indicated as follows: ●, AbSV63; ◆, AbK8; ◇, AbLk26; ▽, AbSV19; ○, AbSV13. Bound ALP activity was measured as change in optical density at 405 nm.

Two monoclonal antibodies, AbSV63 and AbK8, were generated against placental alkaline phosphatase. This has permitted a detailed serological analysis of a large panel of cultured cells. The results of the MHA assays on the cell panel show that SV63 is expressed on choriocarcinoma, teratocarcinoma and a subset of epithelial cancer lines. The pattern of K8 expression represents a subset of the SV63 pattern on the cell panel. In normal tissues, SV63 is found in the placenta (prominent staining of the syncytiotrophoblast and weaker staining of the cytotrophoblast), intestinal epithelium and germ cells, whereas K8 reactivity is restricted to the trophoblast. A subset of teratocarcinomas expressed SV63 (⅜) and K8 (⅜), and SV63 was also found in ¼ colon cancers. The SV63 and K8 antigens were shown to have alkaline phosphatase activity using a solid-phase immunosorbent-assay (FIG. 2). Immunoprecipitation tests with AbSV63 and AbK8 identified the antigens as glycoprotein of molecular weight of about 68,000 daltons, and sequential immunoprecipitation tests with the two antibodies revealed that in GCC-SV(c) cells, the SV63 and K8 epitopes reside on the same molecule.

LK24 antigenic system

6/7 choriocarcinoma cell lines are strong LK24 expressors. LK24 is also present on most breast cancer lines and a small subset of epithelial cancer lines, as well as on EBV-transformed B cells, certain leukemias and lymphomas. However, titration endpoints in MHA tests with breast cancers and lymphoid cells were more than 10-fold lower than with choriocarcinoma cells, and reactivity was limited to a small fraction (5-20%) of cells within a culture. This low percentage of LK24 positive cells, which was not seen with choriocarcinomas, was unaffected by changing the density of the target cells used in MHA tests or the time between target cell plating and testing (1 to 5 days). In normal tissues, LK24 is expressed in the trophoblast, colonic epithelium, distal and collecting tubules of the kidney, urothelium and a subpopulation of cells in the fetal thymus. In the tumor panel, LK24 was found in a variety of epithelial cancers and also in lymphomas. Reactivity of cultured cells with AbLK24 is resistant to boiling (5 min at 100° C.) and trypsin treatment. Immunoprecipitation tests with extracts of [³H]glucosamine and [³⁵S]methionine-labeled cells failed to show any specific components. These biochemical properties suggest that AbLK24 may recognize a carbohydradte or lipid moiety. Type O erythrocytes, but not A, B or AB, remove LK24 reactivity in absorption tests, but no agglutination was seen with either type O or type A, B, and AB erythrocytes. In the ELISA tests AbLK24 failed to show reactivity with any of the purified blood group glycoproteins and glycolipids carrying A, B, H, I, Le$^a$, Le$^b$, X and Y determinants, suggesting that LK24 represents an unrelated antigenic system.

K66 antigenic system

K66 shows an intermediate distribution on the cultured cell panel, being expressed on choriocarcinomas and many epithelial cancer lines, 5/10 astrocytomas, 1/10 melanomas and on normal kidney epithelial cells. Neuroblastomas, EBV-transformed B cells, leukemias, lymphomas and five fibroblast cultures derived from adult skin and lung tissues, were K66 negative. However, two fibroblast cultures derived from fetal tissues were K66 positive. Although K66 reactivity with cultured cells was very strong (e.g., titration endpoints in MHA tests on renal cancer cells $1 \times 10^{-6}$ to $1 \times 10^{-7}$), no reactivity was seen in tests with the normal tissue panel or the tumors. Also, immunoprecipitation tests with extracts of various [³H]glucosamine or [³⁵S]methionine-labeled cells failed to reveal any specific components. Absorption tests showed that the K66 reactivity is destroyed by boiling (5 min at 100° C.) or trypsin treatment of target cells, suggesting a polypeptide.

S4 antigenic system

The S4 antigen, which has been described by Ueda, et al., Proc. Natl. Acad. Sci., U.S.A. 708, 5122–5126 (1981) and Cordon-Cardo, et al., J. Histochem. Cytochem. (in press) (1984), is a marker for normal and malignant kidney epithelial cells. S4 is also expressed on 6/6 choriocarcinoma cell lines. In immunoprecipitation tests, AbS4 precipitates glycoproteins of molecular weight of about 160,000 daltons from both [³H]glucosamine-labeled extracts and ConA-bound fractions of [³⁵S]methionine-labeled extracts of GCC-SV(c), OCC-MM or JEG-3 choriocarcinoma cells, which is consistent with the molecular weight reported for S4 on renal cancer cells. Using unfractioned extracts of [³⁵S]methionine-labeled GCC-SV(c) cells or fractions not bound to ConA-Sepharose, an additional band of molecular weight of 140,000 daltons can be seen on SDS-PAGE. Also, when extracts of GCC-SV(c) were labeled with [³⁵S]methionine in the presence of tunicamycin and used for immunoprecipitation tests, the 140,000 dalton component became more prominent. These results indicate that the 140,000 polypeptide is a precursor for the glycosylated 160,000 molecule.

LK26 is a highly restricted trophoblast antigen. It is found in the placenta (but not in any other normal adult or fetal tissue tested) and is expressed on trophoblastic tumors, including hydatidiform mole and gestational choriocarcinoma. In sharp contrast to the similarity in LK26 expression between normal and malignant trophoblastic cells, normal and malignant kidney epithelial cells differ with respect to this antigen. 15/15 renal cancer cell lines were LK26 positive whereas 5/5 cultures of normal kidney epithelial cells were LK26 negative. Also, tissues of normal adult and fetal kidney lacked LK26, whereas a subset of renal cancer showed the antigen. Thus, the antigen seems to be restricted to normal trophoblastic cells and certain tumors (choriocarcinoma, subsets of other teratocarcinomas, and epithelial cancers).

It has been speculated that some biological properties of cancer cells, e.g., invasion of tissues and metastatic spread, correspond to cellular functions normally expressed by the trophoblast during early stages of development, extinguished in the adult stage, and re-expressed in cancer cells. The pattern of LK26 expression seems provocative in this respect but, clearly, further studies are needed to define the significance of this cell surface antigen. The availability of cultures of normal kidney epithelial cells (LK26 negative) and renal cancer cells (LK26 positive) from the same individuals may provide an in vitro model for these studies.

S4 is a marker of normal and malignant kidney epithelial cells, both in vitro and in tissues. S4 antigen is present on choriocarcinoma cell lines. In this respect, the S4 distribution resembles that of LK26, but the two antigens can be distinguished by their molecular weights and important differences in their serological distribution: both S4 and LK26 are present on malignant kidney epithelial cells and on choriocarcinoma cells but S4 is found on normal kidney epithelial cells and not on normal trophoblastic cells, whereas LK26 is strongly expressed on normal trophoblst, but not on normal kidney epithelial cells.

While S4 and LK26 represent antigens shared between trophoblastic cells and cells of renal origin, a different relationship is found for the other antigens described herein: SV19, SV63 and LK24 are common to trophoblastic cells and colon and/or breast epithelial cells, with SV19 being the most restricted of this group of antigens. Antibodies AbSV63 and AbK8 recognize different epitopes of the PALP molecule, and their patterns of reactivity with the cell panel are quite distinct from the LK26 pattern. The distribution of SV63 and K8 in normal tissues is in agreement with previous histochemical and immunochemical studies on the tissue representation of the different forms of alkaline phosphatase (ALP) which have been defined by their inhibition characteristics and heat stability, e.g., Harris, Harvey Lect. 76 95–124 (1982). At least four members of this enzyme family seem to be controlled by independent gene loci: placental ALP, intestinal ALP, liver/kidney/bone ALP, and germ cell ALP. Monoclonal antibodies to different forms of ALP have been describe by Slaughter, et al., Proc. Natl. Acad. Sci., U.S.A. 78 1124–1128 (1981); Millan, et al., Cancer Res. 42 2444–2449 (1982); Travers and Bodmer, Int. J. Cancer 33 633–641 (1984). The SV63 distribution in tissues indicates that this epitope is shared by the placental, intestinal and germ cell ALPs, but not the liver/kidney/bone form of the enzyme, whereas K8 is specific for the placental isozyme (PALP). Correspondingly, the group of K8 positive cell lines forms a subset of the group of SV63 positive cell lines. PALP is a highly polymorphic enzyme system and monclonal antibodies specific for certain allelic forms of the enzyme have been describe by Slaughter, supra, and Millan, supra.

AbSV63 and AbK7 recognize monomorphic determinants or, at least, common allelic forms. The serological analysis of the breast cancer lines as shown in FIG. 7, shows a striking reciprocal pattern between SV63 expression and expression of two other cell surface antigens, SV19 and P12 (P12 is related to the Lewis X blood group structure). 3/12 breast cancer lines showed an SV63 positive/SV19 negative/P12 negative phenotype, 7/12 cell lines were SV63 negative/SV19 positive/P12 positive and 2/12 lines did not express any of the antigens. No breast cancer line co-expressed SV63 and SV19 or P23. It has been shown, previously, that normal breast epithelium has an SV63 negative/SV19 positive/P12 positive phenotype, and it will be important to determine the significance of these reciprocal antigenic phenotypes of breast cancer cells, especially in relation to hormonal influences on normal breast tissue and with respect to the clinical characteristics of these breast cancer subsets. All three breast cancers studies in the tumor panel had an SV63/ negative/SV19 positive/P12 positive phenotype. However, more tumors must be tested because McDicken, et al., Int. J. Cancer 32 205–209 (1983) have reported the expression of placental-type ALP in primary breast cancer.

Cell surface antigens which are widely distributed on cultured human cells but are undetectable in tissues have been reported by Fradet, et al., Proc. Natl, Acad. Sci., U.S.A. 81 224–228 (1984). K66 belongs to this group of antigens. AbK66 has very high titers when tested in MHA assays on cultured cells (e.g., titration endpoints of $1 \times 10^{-6}$ to $1 \times 10^{-7}$ on kidney epithelial cells). Therefore, low affinity of the antibody or differences in sensitivity between the serological assays used (MHA assay vs. indirect immunofluorescence) are problably not responsible for the observed discrepancy in K66 distribution in vitro and in vivo. Possibly, this discrepancy is related to the presence of antigen only on rapidly proliferating cells or on cells adapted to the growth conditions in vitro. If this is true, an additional explanation is required to account for the clear distinction between K66 positive and K66 negative cell types in vitro, both of which have comparable rates of proliferation. Of particular interest is the finding that among short term cultures of fibroblasts, those derived from adults were K66 negative whereas those derived from fetal tissues were K66 positive.

The antigenic systems described herein, with the exception of PALP, differ from the cell surface antigens and secreted proteins of choriocarcinoma and normal trophoblastic cells that have been studies by other investigators as reported by Lipinski, et al., Proc. Natl. Acad. Sci., U.S.A. 78 5147–5150 (1980); Sunderland, et al., Immunol. 43 541–546 (1981); McLaughlin, et al., Int. J. Cancer 30 21–26 (1982); Travers, et al., Int. J. Cancer 33 633–641 (1984). Four of the previously described monoclonal antibodies to trophoblast antigens were available for a direct serological comparison on a discriminating cell panel as shown by FIG. 8. It is immediately apparent the NDOG-1, NDOG-2, Trop-1, and Trop-2 are different from LK26, SV19, LK24, K66 and S4. However, NDOG-2 and SV63 co-type and may both react with ALP. NDOG-1 did not show any cell surface reactivity with the cell lines used in this study. Both Trop-1 and Trop-2 showed a broader representation on the cell panel and cannot be distinguished from each other as the anti-Trop-2 antibody showed higher reactivity and a serological pattern that overlapped the Trop-1 pattern.

The restriction of antigens LK26, S4, SV19 and PALP to only a small number of normal human tissues make them useful diagnostic markers for gestational choriocarcinomas and germ cell tumors. In addition, the reciprocal expression of SV63 and SV19/P12 in subsets of breast cancers and the presence of LK26 on renal cancer cells (but not normal kidney epithelium) indicate that these antigens may be of interest in the study of other epithelial cancers as well. The highly restricted distribution of LK26, which is undetectable in normal tissues other than the trophoblast, makes this antigen a possible target for immunological imaging and immunotherapy of choriocarcinoma.

Different subsets of the phenotyping panel described, e.g., in FIGS. 4 and 5, may be used. For example, in phenotyping cultured choriocarcinoma cells, FIG. 4 shows that LK26 shows affinity, to one degree or another, with lung, renal, ovarian/uterine, breast, teratocarcinoma, and choriocarcinoma cancer cells, and contacting a cell sample to this mAb would limit the possibilities of the identity of the cell sample accordingly. Further contact with SV19 would eliminate the possibility of the sample being lung, renal, or ovarian/uterine cancer, as SV19 is distributed only on breast, teratocarcinoma, and choriocarcinoma cancer cells. Further contact with MAb K8 would eliminate the possibility of breast cancer cells, and a final contact, with LK24, would identify the cells as either teratocarcinoma or choriocarcinoma. Although LK24 antigen is distributed over more than one cancer cell type, the passage through LK26, SV19, and K8 has limited the cell possibilites to either of choriocarcinoma or teratocarcinoma. Binding to the cells of LK24 indicates choriocarcinoma, no binding indicates teratocarcinoma. Hence, the panel LK26, SV19, K8, and LK24 will determine the presence, or lack thereof, of both choriocarcinoma and teratocarcinoma.

The terms and expression which have been employed are used as terms of description and not of limitation, and there is no intention in the use of such terms and expressions of excluding any equivalents of the features shown and described or poritons thereof, it being recognized that various modifications are possible within the scope of the invention.

TABLE 1

| Cell line | Origin | Monoclonal Antibody | | | | | | |
|---|---|---|---|---|---|---|---|---|
| | | LK26 | SV19 | K8 | SV63 | LK24 | K66 | S4 |
| GCC-SV(c) | Gestational chorioca. | 1000 | 1000 | 1500 | 2500 | 250 | — | 100 |
| Lu-75(c) | Gestational chorioca. | 150 | 150 | 10 | 10 | 50 | 150 | 25 |
| BeWo | Gestational chorioca. | 500 | 50 | 1000 | 1500 | 150 | 50 | 25 |
| JEG-3 | Gestational chorioca. | 150 | 150 | 10 | 1000 | 50 | — | 1 |
| JAR | Gestational chorioca. | 150 | 50 | — | 50 | 150 | — | |
| SCH | Gastric chorioca. | 1000 | 50 | — | 50 | — | — | 250 |
| OCC-MM | Ovarian chorioca. | 500 | 25 | — | 10 | 50 | 3000 | 250 |

Serial dilutions of antibody were tested by MHA assays and the numbers indicate the reciprocal of the highest antibody dilution ($\times 10^{-3}$) giving rosette formation. Dashes indicate negative reactions at the starting dilution of antibody (1/250 nu/nu mouse serum).

TABLE 2

REACTIVITY OF MONOCLONAL ANTIBODIES TO CELL SURFACE ANTIGENS OF CULTURED HUMAN CELLS AND CELL LINES

| Cell lines | Monoclonal Antibody | | | | | |
|---|---|---|---|---|---|---|
| | LK26 | SV19 | K8 | SV63 | LK24 | K66 |
| Choriocarcinoma | | | | | | |
| GCC-SV(c), LU-75(c),BeWo, JAR JEG-3, OCC-MM,SCH | ●●●●● ●● | ●●●●● ●● | ●●●●● 00 | ●●●●● ●● | ●●●●● ●○ | ○●●○○ ●○ |
| Teratocarcinoma | | | | | | |
| Tera-1,-2,833KE,577MF | ●●●● | 0000 | ●●●○ | ●●●○ | ●●●○ | 00●0 |
| Breast cancer | | | | | | |
| MCF-7,Cama,A1Ab,ZR75.1, BT-20,-474,SK-BR-5,-7 MDA-48-134,-231 | ●0000 0C●0● | ●●000 ●0000 | 00000 00000 | 0000● 0000● | ●●●●● ●0000 | C●0●0 ●0●●● |
| Colon cancer | | | | | | |
| SW-48,-403,-480,-620,-837 SW-1083,-1116,-1222,-1217, SC-40-10,-11,-13,-15,HT29 | 00●●0 00000 0000 | 00000 00000 0000 | 00●00 0●000 0000 | 00●●0 C●000 ●C00 | 0●●00 00000 000C | ●●●●● ●0000 ●C●● |
| Ovarian, uterine cancer | | | | | | |
| SK-V08,-2774,A10,ROAC, SW626,KD-UT-1,ME180 | ●0●00 ●0 | 00000 00 | ●0●00 00 | ●0●00 00 | 000●0 00 | ●●●C0 00 |
| Bladder cancer | | | | | | |
| TCCSUP,253J,T24,RT4,486P, VM-CUB-1,-2,-3,639V,647V, SW-800,-1710,575A,SCABER | 00000 ●000● 0●00 | 00000 00000 0000 | 00000 00000 00000 | 0000● ●0●0● 0000 | 000UU 00000 0000 | ●●●C0 ●●●●● ●●●● |
| Renal cancer | | | | | | |
| SK-RC-1,-2,-4,-6,-7, SK-RC-8,-9,-20,-29,-31, SK-RC-34,-39,-41,-44,-45 | ●●●●● ●●●●● ●●●●● | 00000 00000 00000 | 00000 00000 00000 | 00000 00000 00000 | 0C000 000●0 0●C●0 | ●●●●● ●●●●● ●●●●● |
| Prostrate cancer | | | | | | |
| DU-145,KNS-62 | 00 | 00 | 00 | 00 | 00 | ●0 |
| Lung cancer | | | | | | |
| SK-LC-1,-2,05,06,-7, SK-LC-8,-12,-14,-16,-17 | ●0●●0 00●00 | 00000 00●00 | 00000 00000 | 00000 00000 | 0●0●● ●0000 | ●0●C0 000●● |

TABLE 2-continued

REACTIVITY OF MONOCLONAL ANTIBODIES TO CELL SURFACE ANTIGENS OF CULTURED HUMAN CELLS AND CELL LINES

| Cell lines | LK26 | SV19 | K8 | SV63 | LK24 | K66 |
|---|---|---|---|---|---|---|
| Pancreas, hepatic cancer | | | | | | |
| Capan-1,-2,AsPc-1,SK-HEP-1 | 0●00 | 0000 | 0000 | 0●●0 | 0000 | ●●●● |
| Melanoma | | | | | | |
| SK-MEL-12,-23,-28,-29,-31, | 00000 | 00000 | 00000 | 00000 | 00000 | 00000 |
| SK-MEL-37,41,-94,-147,-153 | 00000 | 00000 | 00000 | 00000 | 00000 | 0●000 |
| Astrocytoma | | | | | | |
| SK-MG-1,-2,-3,-14,-6, | 00000 | 00000 | 00000 | 00000 | 00000 | ●0●●0 |
| SK-MG-7,-9,-12,-13,-17 | 00000 | 00000 | 00000 | 00000 | 00000 | 0●●●0 |
| Neuroblastoma | | | | | | |
| SK-N-SH,-MC,-BE(1),-BE(2) | 0000 | 0000 | 0000 | 0000 | 0000 | 0000 |
| Leukemia, lymphoma | | | | | | |
| MOLT-4,T45,HPB-ALL,212, | 00000 | 00000 | 00000 | 00000 | ●●●●0 | 00000 |
| SK-DHL-2,-10,SK-LY-16,-18, | 00000 | 00000 | 00000 | 00000 | 00000 | 00000 |
| RAJI,BALL-1,ARA-10,NALL-1, | 00000 | 00000 | 00000 | 00000 | 00●●● | 00000 |
| NKL-1,-2,NALM-1,-16,HL-60, | 00000 | 00000 | 00000 | 00000 | 0●000 | 00000 |
| K562,SK-MY-1,U937 | | | | | | |
| Normal cells | | | | | | |
| Kidney epithelium | 00000 | 00000 | 00000 | 00000 | 00000 | ●●●●● |
| Skin fibroblasts | 00000 | 00000 | 00000 | 00000 | 00000 | 00000 |
| EBV-transformed B cells | 00000 | 00000 | 00000 | 00000 | ●●●00 | 00000 |
| Erythrocytes (A,B,O) | 000 | 000 | 000 | 000 | 00● | 000 |
| Chriocarcinoma | ●●●●● | ●●●●● | ●●●0● | ●●●●● | ●●●●● | ●000● |
| | ●● | ●● | 00 | ●● | ●0 | ●0 |
| Teratocarcinoma | ●●●0 | 0●●0 | ●●●0 | 0●●0 | 0000 | 00●0 |
| Breast cancer | ●0000 | ●●●00 | 00000 | 0000● | ●●●●● | ●●●C0 |
| Colon cancer | 00000 | 00000 | ●●000 | ●●000 | 00000 | 0●000 |
| Ovary/uterus cancer | ●0000 | 00000 | ●0000 | ●0000 | 0●000 | ●0●00 |
| Bladder cancer | 00000 | 00000 | 00000 | 0000● | 00000 | ●●●00 |
| Renal cancer | 0●●●● | 00000 | 00000 | 00000 | 00000 | ●●●●● |
| Lung cancer | ●0000 | 00000 | 00000 | 00000 | ●0000 | 000●● |
| Melanoma | 00000 | 00000 | 00000 | 00000 | 00000 | 00000 |
| Astrocytoma | 00000 | 0●000 | 00000 | 00000 | 00000 | ●●C00 |
| Neuroblastoma | 00000 | 00000 | 00000 | 00000 | 00000 | 00000 |
| Leukemia/lymphoma | 00000 | 00000 | 00000 | 00000 | ●●●●● | 00000 |
| | 00000 | 00000 | 00000 | 00000 | 00000 | 00000 |
| EBV+ B cells | 00000 | 00000 | 00000 | 00000 | ●●●00 | 00000 |
| Skin fibroblasts | 00000 | 00000 | 00000 | 00000 | 00000 | 00000 |
| Kidney epithelium | 00000 | 00000 | 00000 | 00000 | 00000 | ●●●●● |
| Erythrocytes (A,B,O) | 000 | 000 | 000 | 000 | 00● | 000 |

Serial dilutions of antibody were tested by MHA asays. Reactivity with the cell lines shown is as follows:
●positive reaction with titration endpoint of $1 \times 10^{-4} - 1 \times 10^{-5}$;
0positive reaction with titration endpoint if $4 \times 10^{-3} - 1 \times 10^{-4}$;
0 no reactivity at starting dilution of antibody (i.e., 1/250 nu/nu mouse serum).
Note that LK24 reactivity is restricted to a small fraction (5-20%) of the cells in the cultures.
Human erythrocytes were tested by absorption analysis and hemagglutination tests. AbLK24 reacted with type "O" erythrocytes in absorption tests, but did not produce hemagglutination.

TABLE 3

IMMUNOFLUORESCENCE ANALYSIS OF HUMAN ADULT (A) AND FETAL (F) TISSUES WITH MONOCLONAL ANTIBODIES TO CELL SURFACE ANTIGENS

| | LK26 | | SV19 | | K8 | | SV63 | | LK24 | | K66 | |
|---|---|---|---|---|---|---|---|---|---|---|---|---|
| Tissue | A | F | A | F | A | F | A | F | A | F | A | F |
| Placenta | | | | | | | | | | | | |
| 14 weeks | | ● | | ● | | ● | | ● | | ● | | 0 |
| 40 weeks | | ● | | ● | | ● | | ● | | ● | | 0 |
| Mammary gland | 0 | | ● | | 0 | | 0 | | 0 | | 0 | |
| Colon | 0 | 0 | ● | ● | 0 | 0 | ● | ●● | ● | ● | 0 | 0 |
| Testis | 0 | 0 | 0 | 0 | 0 | 0 | ● | ● | 0 | 0 | 0 | 0 |
| Ovary | 0 | 0 | 0 | 0 | 0 | 0 | ● | ● | 0 | 0 | 0 | 0 |
| Uterus/Cervix | 0 | | 0 | | 0 | | 0 | | 0 | | 0 | |
| Fallopian tube | 0 | | 0 | | 0 | | 0 | | 0 | | 0 | |
| Kidney | 0 | 0 | 0 | 0 | 0 | 0 | 0 | 0 | ● | ● | 0 | 0 |
| Urothelium | 0 | 0 | 0 | 0 | 0 | 0 | 0 | 0 | ● | ● | 0 | 0 |
| Liver | 0 | 0 | 0 | 0 | 0 | 0 | 0 | 0 | 0 | 0 | 0 | 0 |
| Pancreas | 0 | 0 | 0 | 0 | 0 | 0 | 0 | 0 | 0 | 0 | 0 | 0 |
| Lung | 0 | 0 | 0 | 0 | 0 | 0 | 0 | 0 | 0 | 0 | 0 | 0 |
| Bronchus | 0 | 0 | 0 | 0 | 0 | 0 | 0 | 0 | 0 | 0 | 0 | 0 |
| Adrenal gland | 0 | 0 | 0 | 0 | 0 | 0 | 0 | 0 | 0 | 0 | 0 | 0 |
| Thyroid gland | 0 | 0 | 0 | 0 | 0 | 0 | 0 | 0 | 0 | 0 | 0 | 0 |
| Thymus | | 0 | | 0 | | 0 | | 0 | | ● | | 0 |
| Spleen | 0 | 0 | 0 | 0 | 0 | 0 | 0 | 0 | 0 | 0 | 0 | 0 |
| Lymph node | 0 | 0 | 0 | 0 | 0 | 0 | 0 | 0 | 0 | 0 | 0 | 0 |
| Skin | 0 | 0 | 0 | 0 | 0 | 0 | 0 | 0 | 0 | 0 | 0 | 0 |
| Heart/Blood vessel | 0 | 0 | 0 | 0 | 0 | 0 | 0 | 0 | 0 | 0 | 0 | 0 |
| Nervous | 0 | 0 | 0 | 0 | 0 | 0 | 0 | 0 | 0 | 0 | 0 | 0 |

TABLE 3-continued
IMMUNOFLUORESCENCE ANALYSIS OF HUMAN ADULT (A) AND FETAL (F) TISSUES WITH MONOCLONAL ANTIBODIES TO CELL SURFACE ANTIGENS

| | Monoclonal Antibody | | | | | | | | | | | |
|---|---|---|---|---|---|---|---|---|---|---|---|---|
| | LK26 | | SV19 | | K8 | | SV63 | | LK24 | | K66 | |
| Tissue | A | F | A | F | A | F | A | F | A | F | A | F | system

● positive reaction
◐ positive reaction with a subpopulation of cells
0 no reactivity
Note that SV63 reactivity was restricted to germ cells in the testis and ovary tissue examined.
Note that LK24 reactivity was restricted to distal and collection tubules in the kidney tissue examined.

TABLE 4
IMMUNOFLUORESCENCE ANALYSIS OF HUMAN TUMOR TISSUES WITH MONOCLONAL ANTIBODIES

| Tumor type | Monoclonal Antibody | | | | | |
|---|---|---|---|---|---|---|
| | LK26 | SV19 | K8 | SV63 | LK24 | K66 |
| Teratocarcinoma | ●●00 | ●000 | ●0●● | ●0●● | 0000 | 0000 |
| | 0000 | 0000 | 0000 | ●000 | ●●00 | 0000 |
| Choriocarcinoma (gestational) | ● | ● | n.t. | ● | ● | n.t. |
| Hydatidiform mole | ● | ● | n.t. | ● | ● | n.t. |
| Renal cancer | ●000 | 0000 | 0000 | 0000 | 0000 | 0000 |
| Colon cancer | 0000 | ●●00 | 0000 | 0000 | 0000 | 0000 |
| Bladder cancer | 0000 | 0000 | 0000 | 0000 | ●●●● | 0000 |
| Breast cancer | ●00 | ●●● | 000 | 000 | 0●● | .000 |
| Lung cancer | 0000 | ●●00 | 0000 | 0000 | ●0●0 | 0000 |
| Melanoma | 00 | 00 | 00 | 00 | 00 | 00 |
| Astrocytoma | 00 | 00 | 00 | 00 | 00 | 00 |
| Lymphoma | 00 | 00 | 00 | 00 | ●● | 00 |

● positive reaction
◐ positive reaction with a subpopulation of cells
0 no reactivity
Note that SV63 reactivity was restricted to germ cells in the testis and ovary tissue examined.
Note that LK24 reactivity was restricted to distal and collection tubules in the kidney tissue examined.

TABLE 5
REACTIVITY OF MONOCLONAL ANTIBODIES TO CHORIOCARCINOMA ANTIGENS WITH HUMAN BREAST CANCER LINES

| Cell line | Monoclonal Antibody | | |
|---|---|---|---|
| | SV63 | SV19 | P12 |
| MCF-7 | − | ++ | ++ |
| Cama | − | ++ | + |
| BT-474 | − | + | +++ |
| SK-BR-5 | − | + | + |
| ZR75.1 | − | + | ++ |
| MDA-MG-134 | − | + | ++ |
| A1Ab | − | + | ++ |
| MDA-MB-157 | − | − | − |
| SK-BR-7 | − | − | − |
| MDA-MB-231 | +++ | − | − |
| MDA-MB-361 | +++ | − | − |
| BT-20 | +++ | − | − |

Results of MHA assays are indicated as follows:
+++ positive reaction in MHA direct test with titration endpoint of $1 \times 10^{-4} - 1 \times 10^{-7}$;
++ positive reaction in MHA direct test with titration endpoint of $4 \times 10^{-3} - 1 \times 10^{-4}$;
+ positive reaction in absorption tests, but not in MHA direct tests;
− negative reaction in both direct test and absorption analysis.

TABLE 6
COMPARISON OF MONOCLONAL ANTIBODIES TO TROPHOBLAST ANTIGENS

| Cell line | Monoclonal Antibody | | | | |
|---|---|---|---|---|---|
| | NDOG-1 | NDOG-2 | SV63 | Trop-1 | Trop-2 |
| GCC-SV(c),JEG-3,BeWo,833K | 0000 | ●0●● | ●●●● | ●●●● | 0●00 |
| MCF-7,Cama,BT-20 | 000 | 00● | 00● | ●●● | 0●● |
| SK-UT-1,2774,Calu-1,SK-LC-6 | 0000 | 0000 | 0000 | ●●00 | 0000 |
| U251MG,SK-Mel-28,SK-N-SH,-BE(2) | 0000 | 0000 | 0000 | ●000 | 0000 |
| CAPAN-2,SW-403,-48,-620 | 0000 | 000● | 000● | ●0●● | ●000 |
| SK-RC-7,-29,-39,-44,Caki-1 | 00000 | 00000 | 00000 | ●●●●● | 000●0 |
| HPB-ALL,P-12,CCRF-CEM | 000 | 000 | 000 | 000 | 000 |
| NK-1,FB-1 | 00 | 00 | 00 | ●0 | ●0 |

Cell lines were tested by MHA assays. Reactivity is indicated by filled or semi-filled circles, following Table 2. NDOG-1 and NDOG-2 were tested as hybridoma supernatants at 1000-fold lower dilutions. For Trop-1 and Trop-2 ascites fluid from hydbrid clones 162-21.2 and 162.46.2 as in Lipinski, Proc. Natl. Acad. Sci., U.S.A. 78 S147-5150 (1981) were used.

We claim:

1. Hybridoma cell lines produced by fusion of mouse spleen cells immunized with human choriocarcinoma cells or placental membranes with mouse myeloma cells, said hybridomas producing monoclonal antibodies specific for surface glycoproteins of human choriocarcinoma, trophoblast, or teratocarcinoma cells or tissue, said hybridoma cell lines producing monoclonal antibodies LK26, SV19, LK24 and K66.

2. Monoclonal antibodies specific for cell surface glycoproteins of human choriocarcinoma, trophoblast or teratocarcinoma cells or tissue, said monoclonal antibodies selected from the group consisting of LK26, SV19, LK24, and K66.

3. A panel for phenotyping cultured choriocarcinoma or teratocarcinoma cells or tissues comprising at least two monoclonal antibodies of the group consisting of LK26, SV19, LK24, and K66.

4. A method of phenotyping cultured choriocarcinoma or teratocarcinoma cells or cancerous tissue comprising contacting a sample of cell or tissue with a panel of monoclonal antibodies comprising at least two monoclonal antibodies of the group consisting of LK26, SV19, K8, SV63, LK24 and K66 under conditions favoring formation of an immune complex and observing formation of said complex or lack thereof.

* * * * *